(12) United States Patent
Fine et al.

(10) Patent No.: US 7,020,506 B2
(45) Date of Patent: Mar. 28, 2006

(54) METHOD AND SYSTEM FOR NON-INVASIVE DETERMINATION OF BLOOD-RELATED PARAMETERS

(75) Inventors: Ilya Fine, Rehovot (IL); Alexander Finarov, Rehovot (IL); Iosef Gandelman, Ashdod (IL); Boris Fikhte, Rehovot (IL)

(73) Assignee: Orsense Ltd., Rehovot (IL)

( * ) Notice: Subject to any disclaimer, the term of this patent is extended or adjusted under 35 U.S.C. 154(b) by 25 days.

(21) Appl. No.: 10/702,044

(22) Filed: Nov. 6, 2003

(65) Prior Publication Data

US 2005/0101846 A1 May 12, 2005

(51) Int. Cl.
*A61B 5/00* (2006.01)
(52) U.S. Cl. ...................... 600/316; 600/322
(58) Field of Classification Search ........ 600/309–310, 600/335, 316, 547, 322
See application file for complete search history.

(56) References Cited

U.S. PATENT DOCUMENTS

| 4,975,581 | A | * | 12/1990 | Robinson et al. ...... 250/339.09 |
| 5,111,817 | A | * | 5/1992 | Clark et al. ................. 600/323 |
| 5,348,002 | A |   | 9/1994 | Caro |
| 5,582,179 | A | * | 12/1996 | Shimizu et al. ............ 600/485 |
| 5,642,734 | A | * | 7/1997 | Ruben et al. ............... 600/506 |
| 5,792,668 | A |   | 8/1998 | Fuller et al. |
| 5,827,181 | A | * | 10/1998 | Dias et al. .................. 600/322 |
| 5,941,821 | A |   | 8/1999 | Chou |
| 6,049,728 | A |   | 4/2000 | Chou |
| 6,285,894 | B1 | * | 9/2001 | Oppelt et al. .............. 600/322 |
| 6,309,884 | B1 | * | 10/2001 | Cooper et al. ............... 436/14 |
| 6,400,972 | B1 | * | 6/2002 | Fine ............................ 600/322 |
| 6,466,806 | B1 |   | 10/2002 | Geva et al. |
| 6,587,704 | B1 | * | 7/2003 | Fine et al. .................. 600/335 |
| 2002/0155615 | A1 |   | 10/2002 | Novikov et al. |

FOREIGN PATENT DOCUMENTS

| EP | 0 282 234 | 9/1988 |
| WO | WO 00/43759 | 7/2000 |
| WO | WO 01/45553 | 6/2001 |
| WO | WO 01/96872 | 12/2001 |
| WO | WO 02/069791 | 9/2002 |

* cited by examiner

Primary Examiner—Eric F. Winakur
(74) Attorney, Agent, or Firm—Nath & Associates PLLC; Lee C. Heiman; Viviana Amzel (57) ABSTRACT

A method and system for measuring time variations of a response of a blood perfused fleshy medium to an external electromagnetic field is provided. The response of the medium to the external electromagnetic field can be a photo-acoustic signal, obtained in response to the exciting light, and/or impedance of the medium, in response to the applied ac electromagnetic field. Measurements of the time variations of the response of the medium are carried out when the condition of artificial kinetics is created and maintained over a certain time period by applying primary over-systolic pressure to a certain location at the medium with normal blood flow, so as to achieve a state of temporary blood flow cessation at the medium downstream of the certain location. When required, the control of the condition of the artificial kinetics can be further achieved by applying a perturbation of secondary pressure to the fleshy medium.

35 Claims, 4 Drawing Sheets

METHOD AND SYSTEM FOR NON-INVASIVE DETERMINATION OF BLOOD-RELATED PARAMETERS

FIELD OF THE INVENTION

This invention relates to techniques for non-invasive measurements of blood-related parameters, and in particular, to methods and systems for measuring blood characteristics by photo-acoustic and electrical measurement techniques.

BACKGROUND OF THE INVENTION

Non-invasive techniques for measuring various blood parameters, e.g. the concentration of glucose in blood, blood oxygen saturation, etc. have become very popular, since they do not require the withdrawal of a blood sample from a patient's body. One approach for non-invasively determining the composition of blood makes use of the interaction of electromagnetic radiation with the blood under examination. It is known that electromagnetic radiation having appropriate characteristics may interact with blood in two primary ways. As it passes through a fleshy medium, the radiation is scattered and a portion of it will be absorbed. Different chemical species of the blood scatter and absorb to different degrees at different wavelengths. The physical composition of the fleshy medium will also effect its interaction with the radiation.

A number of methods have been proposed that use optical radiation to probe a patient's body (e.g., a finger) with the goal of determining the concentration of a component of the material.

For example, optical monitoring techniques can utilize the detection of light transmitted or reflected from the location on the patient's body under measurement, and are based on spectrophotometric measurements enabling the indication of the presence of various blood constituents based on known spectral behaviors of these constituents. Usually, the optical monitoring techniques utilize a measurement optical device or probe attached to the patient's finger, and include an optical assembly for irradiating the finger with light and detecting its light response. For example, the conventional device of the kind specified, such as a pulse oximeter, which is the generally accepted standard of everyday clinical practice, provides for measuring enhanced optical pulsatile signals caused by the changes in the volume of blood flowing through a finger.

It is known that for some blood parameters other than oxygen saturation, e.g., glucose concentration, significant difficulties have been encountered, because their absorption spectral behavior in red and near infrared regions is not as remarkable perceptible as for the oxygenized hemoglobin. Hence, the main limitations of the non-invasive optic techniques other than pulse oximetry are associated with the limited selectivity of the absorption based method.

Another optical technique is disclosed in U.S. Pat. No. 6,400,972, International Applications WO 01/45553 and WO 01/96872, all assigned to the assignee of the present application. This is an occlusion-based technique, according to which over-systolic pressure is applied to the blood perfused fleshy medium with a normal blood flow so as to create a state of temporary blood flow cessation at the measurement location. The measurement with different wavelengths of incident radiation and/or different polarization states of detected light are carried out at sessions which are separate in time and taken during a cessation time period, i.e., when the state of blood flow cessation is maintained. This technique utilizes the condition of "artificial blood kinetics" rather than "natural blood kinetics" taking place when the state of total blood cessation is not achieved. As a result of the cessation of blood flow, a condition of artificial kinetics is achieved with the optical characteristics of the blood associated with the light response being different from those of natural blood kinetics. Indeed, it is known that the scattering properties of blood depend on the size and shape of scatterers (aggregates). Thus, time changes of the light response at the condition of artificial kinetics depend on the changes in the shape and average size of the scattering centers in the medium, i.e., red blood cells (RBC) aggregation (Rouleaux effect). It was found that owing to the effect of artificial kinetics, the optical characteristics of blood changes dramatically, such that they differ from those of the fleshy medium with a normal blood flow by about 25 to 45%, and sometimes even by 60%. Hence, the accuracy (i.e., signal-to-noise ratio) of the technique based on artificial kinetics, as well as selectivity of the optical measurements, can be substantially better when compared with those based on measurements of blood parameters at natural kinetics.

Figure 1:
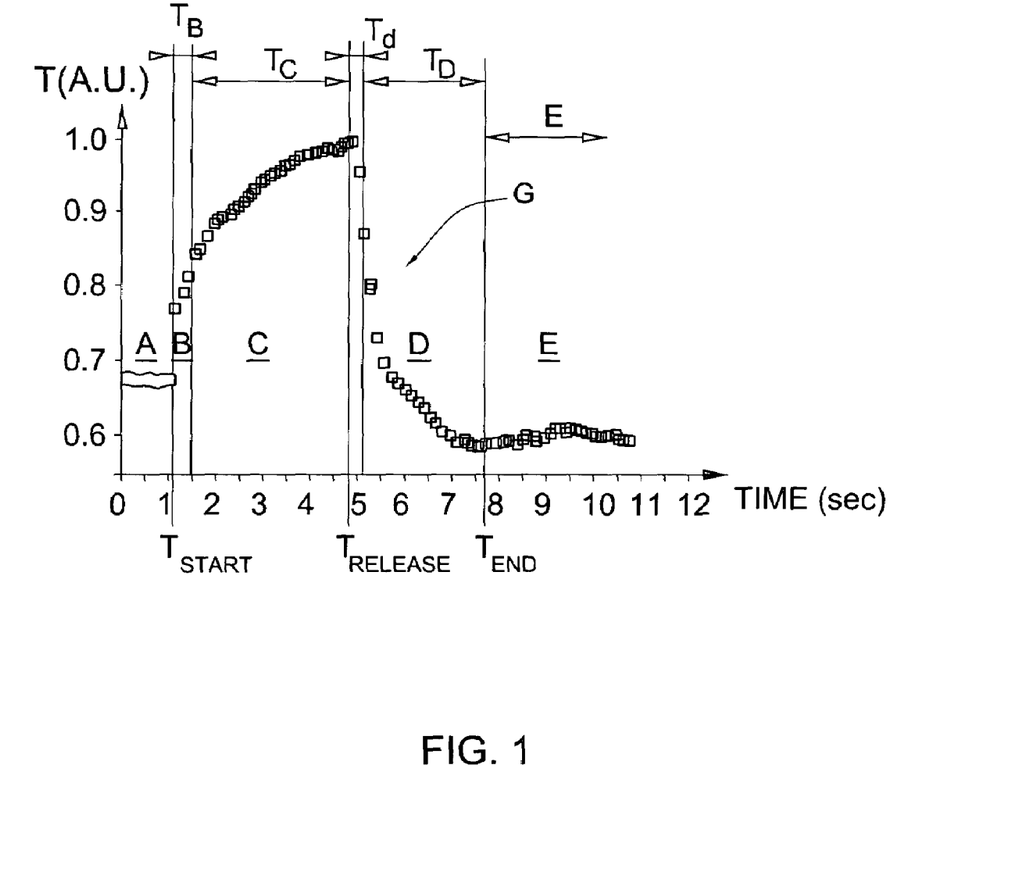
FIG. 1 illustrates a typical plot representing light transmission characteristics of blood obtained when the condition of artificial kinetics is created and changed.

FIG. 1 illustrates an example showing a typical plot representing light transmission/absorption characteristic (light responses) of blood obtained over the time interval when the condition of artificial kinetics is created, maintained during a certain cessation time, and then released. In particular, the plot shows how the light-transmitting characteristic of blood changes under the application and release of the primary over-systolic pressure. The transmitting characteristics are shown in FIG. 1 in Transmission Arbitrary Units (T.A.U.).

The application of primary pressure to the fleshy medium starts at a moment $T_{start}$, and is maintained for a period of time so as not to cause irreversible changes in the medium (e.g., 4 seconds). The pressure is released at the moment $T_{release}$. Measurements of the Relative Transmission are performed continuously, starting prior to the application of the over-systolic pressure. Different regions of light responses of the medium, designated A, B, C, D and E, corresponding to the different states of the blood flow are observed. Region A corresponds to a state of normal blood flow before the over-systolic pressure is applied. As shown, this region is characterized by a standard fluctuating value of the relative light transmission of blood. Region B starts at moment $T_{start}$ (when the pressure is initially applied) and maintains over a short period of time $T_B$ (about 0.5 sec) following the actual start of the condition of artificial blood kinetics. Measurements taken over this time period are not steady and can be disregarded, due to the unavoidable influence of motional and/or other factors causing non-monotonic fluctuations of the light transmission. Region C corresponds to a state of the temporary cessation of blood flow, which lasts within a cessation time $T_C$ between a moment determined as $(T_{start}+T_B)$ and the moment $T_{release}$. During this cessation time, $T_C$, the ascending curve (as shown in FIG. 1) or descending curve (not shown), depending on the incident wavelength of relative light transmission of blood, can be observed. It should be noted that this is the region where the condition of artificial kinetics is maintained over $T_C$. Generally, the light transmission curve can reach an asymptotic maximum over one second to several minutes. Region D corresponds to a transitional state of blood flow, which takes place after releasing the over-systolic pressure. This state starts with a slight delay $T_d$ (approximately 0.5 sec), i.e., at the moment determined as $(T_{release}+T_d)$. During the time period $T_D$ of the duration of region D, the relative transmission of blood monotonously descends until it reaches values characteristic of the normal blood flow. Such a moment is marked as $T_{end}$ in the drawing. Usually, the end of region D, and the beginning of region E, is detected when the changes of the light transmission become periodic and minimal (about 2%). Region E corresponds to a state of the normal blood flow, which is similar to that in region A.

It has also been shown in the prior art that photo-acoustic laser spectroscopy can be used for measuring glucose concentration in blood. In this technique, a laser beam is used to rapidly heat a sample generating an acoustic pressure wave produced in a sample, where the excitation beam is absorbed, that can be measured by high-sensitivity ultrasonic detectors such as piezo-electric crystals, microphones, optical fiber sensors, laser interferometers or diffraction sensors. Prior art techniques for non-invasive measurement of blood glucose by photo-acoustic spectroscopy are described, for example, in U.S. Pat. No. 5,348,002 to Caro; U.S. Pat. No. 5,941,821 to Chou; and U.S. Pat. No. 6,466,806 to Geva, et. al.

U.S. Pat. No. 5,348,002 to Caro discloses a technique for measuring blood glucose which includes a light source for applying electromagnetic radiation to patient's finger under analysis and a transducer for detecting acoustic energy. The transducer is positioned on one side of the finger and the incoming electromagnetic wave impinges on the other side of the finger, opposite the transducer.

The main disadvantage of this technique is that a tissue, such as a body part, is optically thick. The impinging electromagnetic energy is almost totally absorbed by the tissue. Consequently, the measured acoustic wave will respond to the total incident electromagnetic energy, rather than to the fraction absorbed by the glucose.

Moreover, it is well known that the water content in skin or blood can be more than 70%, making water the main absorbing substance. The effect of strong water absorption is twofold. First, because tissue has a high percentage of water, water absorption can prevent a light beam from penetrating a sufficient depth through tissue. Second, water absorption can yield an acoustic signal which is overwhelming compared to that of glucose. The technique disclosed in U.S. Pat. No. 5,348,002 fails to address the adverse effects caused by the absorption of radiation by water, rather than the medium to be measured, such as glucose.

Another photo-acoustic method for non-invasive monitoring of glucose is described in U.S. Pat. No. 5,941,821 to Chou, in which an excitation source provides electromagnetic energy at a wavelength corresponding to the absorption characteristics of the analysis. Upon irradiation, acoustic energy is generated in a relatively thin layer of the sample to be measured, characterized by a heat-diffusing length. The acoustic emission is detected with a differential microphone, one end of which is positioned in a measuring cell and the other end of which is positioned in a reference cell. A processor determines the concentration of the substance being measured based upon the detected acoustic signal. In order to determine the concentration of glucose in the bloodstream, the excitation source is preferably tuned to the absorption bands of glucose in spectral ranges from about 1520–1850 nm and about 2050–2340 nm to induce a strong photo-acoustic emission. In these wavelength ranges, water absorption is relatively weak and glucose absorption is relatively strong. Thus, even though a tissue may have a high percentage of water at the above-specified wavelength ranges, the electromagnetic radiation is able to penetrate through the tissue to a sufficient depth to allow for measurements.

U.S. Pat. No. 6,466,806 to Geva, et. al describes a method and apparatus of resonant photo-acoustic spectroscopy (RPAS) for determining a concentration of an interest component in a medium. The method comprises irradiating a surface of the medium with a light pulse-train comprising equidistant short pulses having variable duration, frequency, number, and power. The frequency of the light short pulses is chosen equal to a natural acoustic oscillation frequency in a medium for resonant light-excitation of acoustic modes. The wavelength of the light pulses is selected so as to excite resonant acoustic oscillation in the medium due to the absorption of light by the interest component and subsequent adiabatic temperature rise in the testing area of the medium.

Some of the non-invasive methods of determining the concentration of the chemical of interest (e.g., glucose) in blood are based on measuring impedance (total electrical resistance) or a component of the impedance of a body part of a patient. For example, U.S. Pat. No. 5,792,668 to Fuller, et al., describes a technique in which two electrodes are brought into direct contact with the human body and real and imaginary components of reflected and/or transmitted electromagnetic Signals are spectrally examined as a function of frequency to identify the concentration of the chemical of interest. The examination can include the analysis of the effective complex impedance presented by the human body, and/or the effective phase shift between the transmitted and reflected signal at the human body.

It is known that the total electrical impedance of a human body, as well as the components of the total electrical impedance, depend not only on the actual value of the concentration of glucose in blood, but also on the temporal rate of change of that concentration. The rate of change of the glucose concentration is specific to each individual and varies within certain limits depending on a number of reasons and factors, such as, for example, environmental, psycho-physiological, nutritional, specific metabolic factors and others.

International Publication No. WO02069791 to Schrepfer, et. al. discloses a technique for determining the concentration of a substance in body liquid. In one of the embodiments, WO02069791 describes a device suited for in-vivo measurements of the human body. The device comprises an elongate electrode having a width much smaller than its length. A holder is provided to mount the electrode to an arm or a leg with the longitudinal axis of the electrode extending parallel thereto. In this way, a large interaction space is established, which allows to measure the desired concentration with a higher level of accuracy. The method of determining the glucose concentration comprises the steps of arranging a first electrode, which is electrically insulated from the specimen, applying a modulated electrical voltage having a frequency between 10 MHz and 2 GHz to the first electrode for generating a modulated field in the specimen and measuring parameters that depend on the electrical impedance of the specimen.

U.S. Patent Application Publication No. 2002/0155615A1 to Novikov, et. al. describes a method of non-invasive determination of a glucose concentration in blood based on the measurements of the total impedance of the skin of a patient taking into account the rate of change of the glucose concentration. The method is based on a linear model of a first order correlation between the glucose concentration and the total impedance. The determination of the concentration of glucose $G(t)$ in blood comprises measuring the total impedance $N(x)$ or a component of the total impedance of the skin, and then determining the concentration of glucose in accordance with the following approximating equation:

$$G(t) = G_1\exp(-a_0 t) + q + a_1\exp(-a_0 t)\int_0^t N(x)\exp(a_0 t)\,dx,$$

where $G_1 = G_0 - q$;

$G_0$ is the initial concentration of glucose in blood at the beginning of the measurement process, q is a parameter that characterizes the ability of a human organism to maintain homeostasis relative to the glucose concentration in blood, $a_0$ is a coefficient that characterizes the correlation between a total electrical impedance (or its components) of the skin and a concentration of glucose in blood of a specific individual, and $a_1$ is a coefficient taking into account the variability of the external factors and specific characteristics of an individual. The coefficients q, $a_0$ and $a_1$ used in an approximating function are determined at the preliminary stage measurements by an invasive method.

SUMMARY OF THE INVENTION

Despite their potential, the known photo-acoustic and impedance methods suffer from limited accuracy. The present invention facilitates non-invasive measurement of blood parameters by providing a novel method and device for measuring time variations of a response of the blood perfused fleshy medium (e.g., finger) to an external electromagnetic field. According to one embodiment, the response to the external electromagnetic field is a photo-acoustic signal obtained in response to the exciting light. According to another embodiment, the response to the external field is the impedance of the medium in response to the applied ac electromagnetic field.

It should be noted that in the present description, the term "impedance" hereinafter will, for brevity, include not only total electrical resistance, but also each component of the impedance. The measured components of the impedance of the medium can, for example, be as follows: an active component, a reactive component, a phase angle between the active and reactive components of the impedance, as well as parameters that can be derived from the impedance and its components. These parameters include, inter alia, dielectric permittivity, dielectric losses and conductivity of the medium.

For both techniques (photo-acoustic and impedance measurements), the invention utilizes the benefits of occlusion-based measurements described above in connection with optical measurement techniques. Namely, the measurement of time variations of the response of the blood perfused fleshy medium by occlusion-based techniques is based on creating and controlling the artificial blood kinetics in the medium. The condition of artificial kinetics is created and maintained for a certain time period by applying primary over-systolic pressure to a certain location at the medium with a normal blood flow so as to achieve a state of temporary blood flow cessation at the medium downstream of the certain location. When required, the control of the condition of the artificial kinetics can be further achieved by applying a perturbation of a secondary pressure to the fleshy medium.

There is thus provided according to one broad aspect of the invention a non-invasive method for use in determination of at least one desired characteristic of blood of a patient, the method comprising:

(a) creating a condition of artificial blood kinetics at a measurement location in a patient's blood perfused fleshy medium and maintaining this condition for a certain time period;

(b) applying an external electromagnetic field to the measurement location;

(c) detecting a time response of the medium from at least a portion of the measurement location to said external electromagnetic field; and (d) generating measured data indicative of time evolutions of the response of the medium over at least a part of said certain time period;

wherein the response to said external electromagnetic field includes at least one of the following:

an acoustic response to illuminating incident light having a wavelength in a range where the scattering properties of blood are sensitive to light radiation, and an impedance of the portion of the medium.

The method further comprising:

(e) analyzing said measured data for determining at least one characteristic parameter derived from said time response of the medium;

(f) providing predetermined reference data sensitive to patient individuality and indicative of the desired blood characteristic obtained by another independent method as a function of said characteristic parameter; and (g) utilizing the determined characteristic parameter derived from said time response of the medium and said predetermined reference data for obtaining a value of the desired blood characteristic.

According to another broad aspect of the invention there is provided a system for non-invasive determination of at least one desired characteristic of blood of a patient, the system comprising:

(i) a pressurizing assembly arranged for creating a condition of artificial blood kinetics at a measurement location in a patient's blood perfused fleshy medium and at least maintaining this condition for a certain time period;

(ii) a measuring probe including a source of an external electromagnetic field configured for applying said external electromagnetic field to said measurement location, and a detecting module configured for detecting a time response of the medium from at least a portion of the measurement location to said external electromagnetic field; and (iii) a control unit electrically coupled to said pressurizing assembly, said control unit including:

a memory for storing reference data sensitive to patient individuality and indicative of the desired blood characteristic as a function of a characteristic parameter derived from said time response; and a data acquisition and processing utility coupled to the detecting module for receiving and analyzing measured data therefrom and configured to utilize the reference data and determine said at least one desired blood characteristic.

The pressurizing assembly includes a primary occlusion cuff for applying primary over-systolic pressure to the fleshy medium at a primary pressure location. When required, the pressurizing assembly can include a secondary occlusion cuff for applying secondary pressure to the fleshy medium at a secondary pressure location, thereby altering the condition of the artificial blood kinetics at the secondary pressure location over a predetermined time interval within said certain time period, so as to modulate properties of the blood affecting the time response.

The primary pressure location can be selected upstream of the secondary pressure location with respect to the normal blood flow direction in the medium. The secondary pressure location can be in the vicinity of the measurement location.

According to one embodiment, the measuring probe can be a photo-acoustic system, where the source of the external electromagnetic field can be configured for generating a light beam in the wavelength range where the scattering or absorbing properties of the patients blood are sensitive to provide an acoustic response, and the detecting module is an acoustic detector. According to another embodiment, the measuring probe can be a system for measuring impedance of at least a portion of the medium at the measurement location.

According to one embodiment, the reference data can be a calibration curve defining a dependence of the characteristic parameter on the desired blood characteristic. The characteristic parameter can, for example, be an actual value of the time response at a certain moment during said certain time period. The certain moment can be chosen when the response attains its near asymptotic magnitude.

According to another embodiment, the characteristic parameter can be a parametric slope defined as a ratio between a first function depending on a time response of the medium corresponding to a first frequency of the external electromagnetic field and a second function depending on the time response of the medium corresponding to a second frequency. According to one example, the first and second functions can be logarithmic functions of the response corresponding to the first and second frequencies, respectively. According to another example, the first and second functions can be a time rate of the changes of the response corresponding to the first and second frequencies, respectively.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

The principles and operation of the system and method for non-invasive measurement of blood parameters according to the present invention may be better understood with reference to the drawings and the accompanying description, it being understood that these drawings and examples in the description are given for illustrative purposes only and are not meant to be limiting. The same reference Roman numerals and alphabetic characters will be utilized for identifying those components which are common in the system for non-invasive measurement of blood parameters shown in the drawings throughout the present description of the invention.

According to one general aspect, the present invention provides a novel method for non-invasive electromagnetic scattering determination of glucose. It should be understood that the present invention is not limited to the measurement of blood glucose levels, but may also be utilized to measure other blood characteristics. Examples of the blood characteristics include, but are not limited to the concentration of a substance in patient's blood (e.g., glucose, hemoglobin), oxygen saturation, Erythrocyte Sedimentation Rate (ESR) and Erythrocyte Aggregation Rate (EAR).

The method is based on creating and, when required, controlling the artificial blood kinetics in a patient's blood perfused fleshy medium, e.g., his finger, and applying photoacoustic and impedance measurements thereto. The condition of artificial kinetics is created and maintained for a certain time period. The creation of the condition of artificial kinetics is preferably made by applying a primary over-systolic pressure to a certain location at the medium with a normal blood flow so as to achieve a state of temporary blood flow cessation, as described above in the background section.

According to the invention, when required, control of the condition of the artificial kinetics can be carried out by applying a perturbation of a secondary pressure to the fleshy medium, as will be described in detail hereinbelow.

According to one embodiment of the invention, the controllable altering of the condition of the artificial blood kinetics is performed by applying a perturbation to the medium by a secondary pressure pulse of a predetermined value over the predetermined time interval so as to modulate scattering/absorbing properties of blood. According to one example, the secondary pressure can be applied to the medium (e.g., patient's finger) at the location of the main occlusion providing the over-systolic pressure. According to another example, the secondary pressure can be applied to the medium at a certain location selected downstream of the main occlusion with respect to the blood flow direction. It should be noted that the location of the application of the secondary pressure may either coincide with the location of a response signal detector or slightly differ from it, depending on the kind of measured medium and/or design of the measurement probe. The physical effect of the secondary pressure results, inter alia, in the modification of the aggregates of red blood cells (RBC). Therefore, the location of the application of the secondary pressure has to be in the vicinity of the measurement place.

The altering of the condition of artificial blood kinetics includes applying a perturbation to the medium by at least one secondary pressure pulse of a predetermined value over a certain time period which is insufficient for irreversible changes in the fleshy medium. The predetermined value of the secondary pressure pulse can, for example, be in the range of about 0–300 mmHg. It was also found by the inventors that one can obtain some more useful information about the patient's blood characteristics by means of manipulating the magnitude of the secondary pressure pulse. In particular, in the case when the magnitude of the secondary pressure pulse is small and does not exceed a certain relatively small value $P_1$, all three main components of the blood (venous, capillary and arterial blood components) can contribute to the measurements. However, in the case when the magnitude of the secondary pressure exceeds the value of $P_1$ the venous blood component can be excluded from the consideration. Likewise, in order to exclude from the consideration also the capillary blood component, the secondary pressure should exceed the value of $P_2$ (where $P_2 > P_1$). In other words, when the magnitude of the secondary pressure is over $P_2$ venous and capillary blood becomes forced out of the measurement location, while arterial blood remains at the measurement location, and measurements in this case would be applied to arterial blood only. It should be understood that the values of $P_1$ and $P_2$, depend on the person's physiology, and should be selected individually for each patient.

A modification of RBC clusters resulting in the altering of the artificial kinetics can be caused by many different ways. Thus, other than the single secondary pulse described above, the altering of the condition of artificial blood kinetics can be carried out by applying a perturbation to the medium by means of the secondary pressure of a predetermined cyclic pattern over the predetermined time interval. The predetermined cyclic pattern can, for example, be in the form of a train of short secondary pressure pulses having a duration of about 0.5–2 seconds and amplitude in the range of about 0–300 mmHg.

According to one embodiment of the invention, the non-invasive measurements are carried out by illuminating a measurement location on the medium at the state of temporary blood flow cessation with an incident light beam, and detecting acoustic energy as a response to the incident electromagnetic energy (light in this case). The light beam is usually a pulsed laser signal having the wavelength selected from a range where the scattering or absorbing properties of blood are sensitive to provide an acoustic response (e.g., 1500–1700 nm).

According to Beer's law, the optical absorption coefficient, and consequently the corresponding photo-acoustic signal, are proportional to the concentration of the component of interest in the medium being tested. Moreover, changes of the absorption/scattering properties of the blood due to the altering of the artificial kinetics will also be reflected on the corresponding photo-acoustic response.

Figure 2:
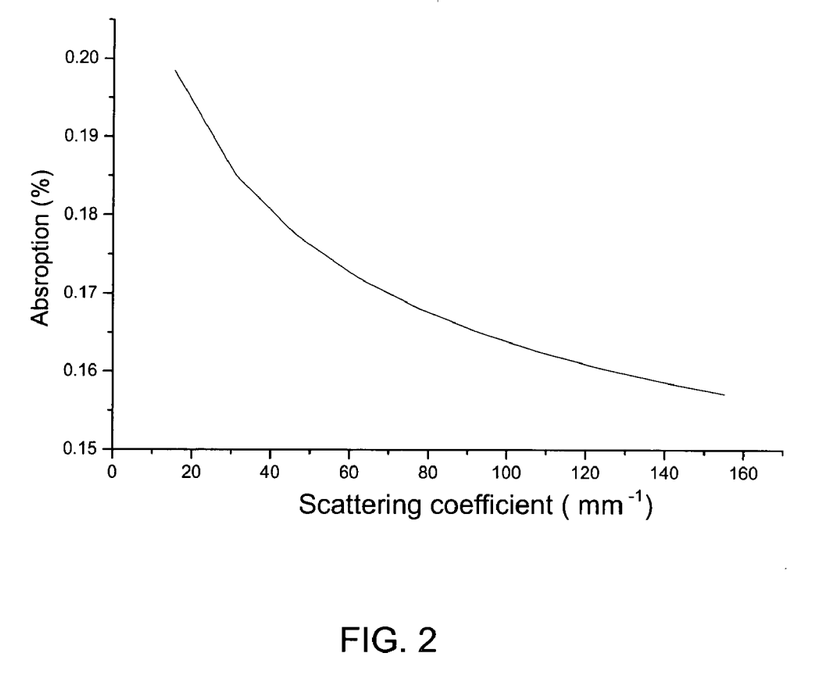
FIG. 2 illustrates an example of the computer simulation of the scattering coefficient of the blood versus the light absorption changes during the condition of the artificial kinetics.

FIG. 2 illustrates an example of the computer simulation of the light absorption changes versus the scattering coefficient of the blood, when the condition of the artificial kinetics changes over time, for example, due to the cessation of blood flow (caused by the described above occlusion maneuver). The computer simulations were carried out for a blood layer of 1 mm thickness, with Hematocrit 0.4 and a light wavelength of 900 nm. It was assumed that at the beginning of the aggregation process, the red blood cells (RBC) were all in a non-aggregated state (e.g., individual red blood cells) that corresponds in this example to the scattering coefficient of single red blood cells, viz. 100 $mm^{-1}$. As can be seen, the changes of the artificial blood kinetics results in the increase of absorption, due to the prolongation of the optical path.

Figure 3:
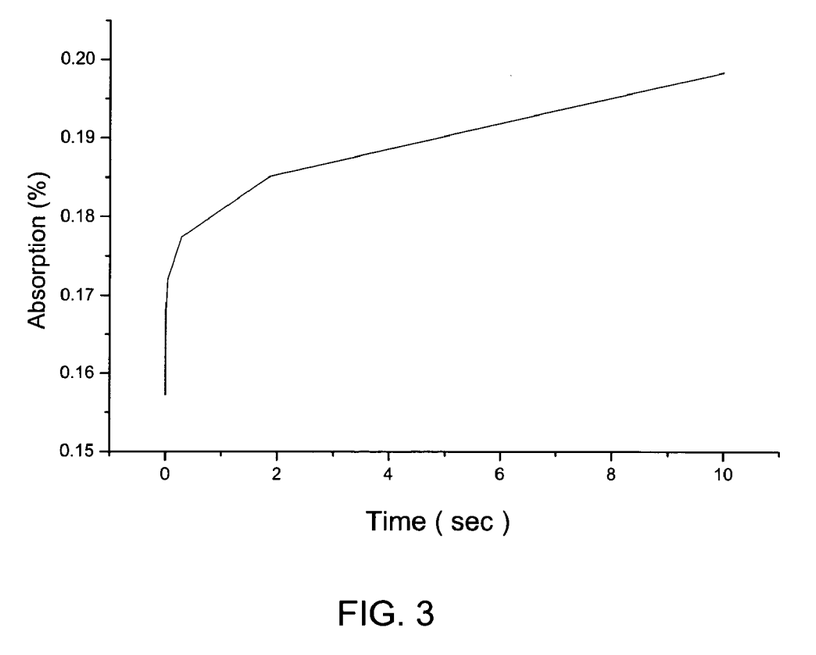
FIG. 3 illustrates time behavior of light absorption in the above computer simulation caused by the artificial blood kinetics.

FIG. 3 illustrates the time behavior of light absorption in the above computer simulation caused by changes in the artificial blood kinetics. As can be appreciated, the prolongation of the optical path, owing to the RBC aggregation, consequently, causes the reduction of light absorption.

Figure 4:
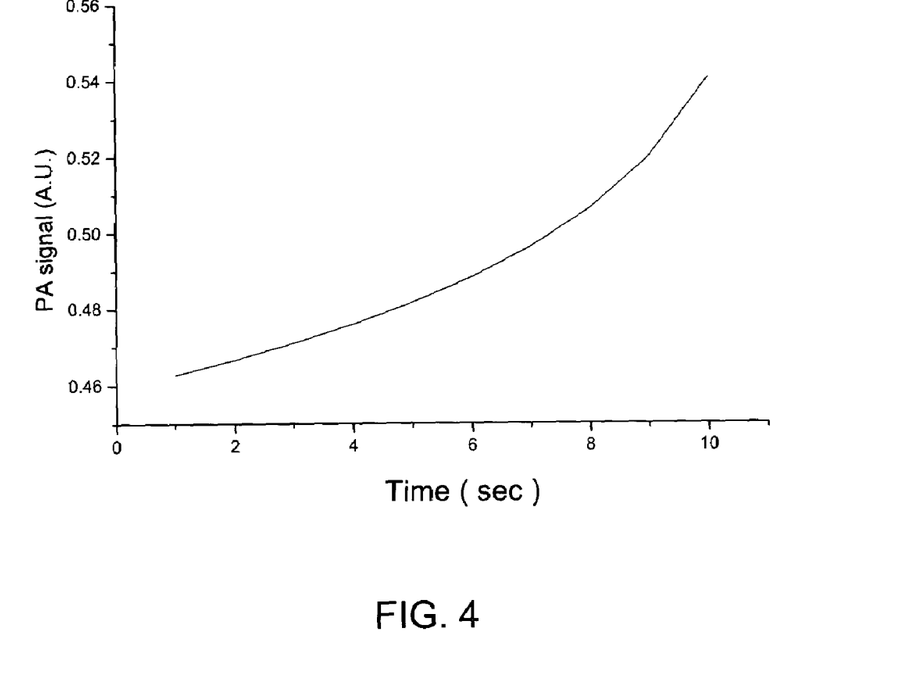
FIG. 4 illustrates time dependence of a typical PA signal (normalized value) obtainable during the condition of artificial blood kinetics.

In turn, a photo-acoustic response is proportional to the light absorption and the scattering coefficient of blood. FIG. 4 illustrates a time dependence of a typical PA signal (normalized value) obtainable during the condition of artificial blood kinetics (i.e., RBC aggregation process). The wavelength of the illumination light for this simulation corresponds to 900 nm.

It should be appreciated that a curve of the corresponding time dependence can also be obtained for a photo-acoustic signal when the condition of the artificial blood kinetics is controllably altered by applying a perturbation to the flesh medium by a predetermined secondary pulse, as described above. In particular, the measured data of the photo-acoustic signal over a certain time interval selected from the intervals when the secondary pressure is applied can be used. Moreover, the measured data over a certain interval selected from the time intervals after the release of the secondary pressure can also be utilized for determining blood characteristics.

According to another embodiment of the invention, the response to the external electromagnetic field is the impedance of the medium in response to the applied ac electromagnetic field. For example, the basic principles of Time Reflection Spectroscopy or Time Domain Dielectric Spectroscopy (see, for example, Yu. Feldman etc., "Time Domain Dielectric Spectroscopy: An Advanced Measuring System." Rev. Sci. Instrum., 1996, V. 67, (9), P. 3208–3216) can be used for determination of the impedance.

It should be noted that components of the impedance or parameters that can be derived from the impedance or its components also can be utilized as a response to the external electromagnetic field. The measured components of the impedance of the medium can be the following: an active component, a reactive component, or a phase angle between the active and reactive components of the impedance. These componets allow to derive, inter alia, such parameters as dielectric permittivity, dielectric losses and conductivity of the medium.

Figure 5:
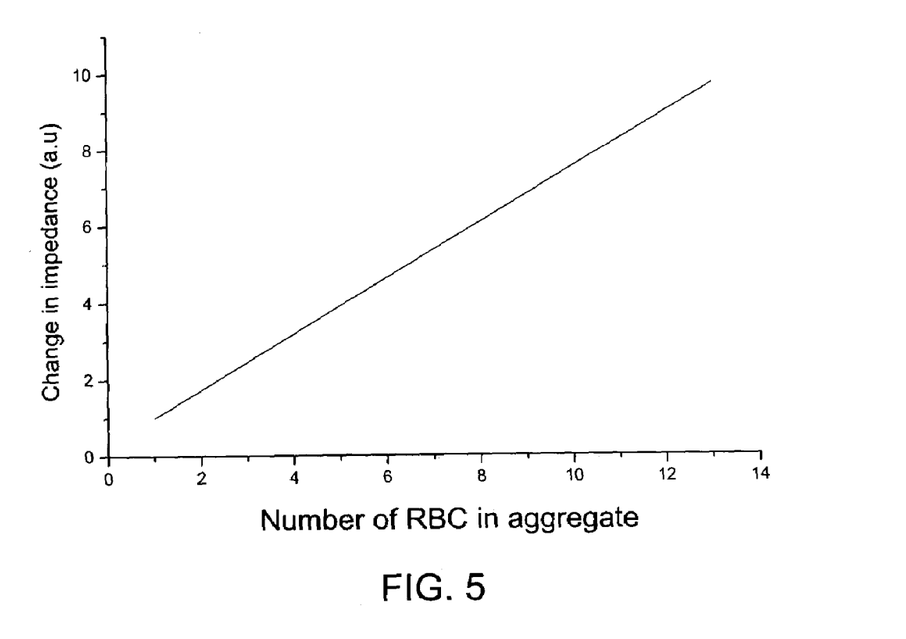
FIG. 5 illustrates an example of a time dependence of a typical impedance signal obtainable during the condition of artificial blood kinetics.

It is well known that dielectric properties of RBC depend on the glucose concentration. In particular, it was measured that impedance of the blood can increase by 0.25 ohm when the glucose level increases by 10 mg/dl. Since this effect is mainly related to the cellular membranes, then the change of the RBC's membranes surface during the aggregation caused by the artificial kinetics should lead to a change in the measured impedance signal. It can be assumed that the impedance signal is proportional to the free surface of RBCs. Thus, the aggregation of N RBCs will approximately reduce the free surface by factor $(N+r/h)/(1+r/h)$, where r and h are the radius of the RBC and the RBC's membrane thickness, respectively. In calculations, r and h can, for example, be set to 4 micron and 1 micron, respectively. Accordingly, the measured entire blood impedance should be varied due to the aggregation process. An example of a dependence of a typical impedance signal versus Number of RBC in an aggregate obtainable during the condition of artificial blood kinetics (i.e., RBC aggregation process) is shown in FIG. 5.

The rate of change of the impedance during the state of the artificial kinetics is specific to each individual and can be used for obtaining the corresponding glucose concentration.

Hence, the accuracy (i.e., signal-to-noise ratio) of the technique based on the artificial kinetics can be substantially better when compared to those based on measurements of the blood parameters at natural kinetics.

Moreover, when required to further increase the sensitivity, the altering component of the impedance (associated with the aggregation) can be easily extracted from the total blood impedance that includes also the components of impedance which are insensitive to the aggregation process, e.g., the components related to skin, water, swear, etc.

It should be appreciated that a certain curve of the corresponding time dependence can also be obtained for impedance when the condition of the artificial blood kinetics is controllably altered by applying a perturbation to the flesh medium by a predetermined secondary pulse, as described above. In particular, for determining blood characteristics the entire impedance or its component (measured data) can be used measured over a certain interval selected from the intervals when the secondary pressure perturbations are applied. Moreover, the measured data over a certain interval selected from the time intervals after the release of the secondary pressure perturbations can also be utilized.

According to the invention, for the determination of blood characteristics, a characteristic parameter should be used derived from the time variations of the response (photo-acoustic signal and/or impedance) of the medium during either the condition of the artificial blood kinetics or when this condition is altered by the secondary pressure perturbations. Since the determination of this parameter does not depend on the details of the employed technique and is similar for the response obtained from either photo-acoustic or impedance measurement techniques, the examples of the procedures for determination of blood characteristics (e.g., glucose concentration) will be shown herebelow for the response corresponding to the generalized case.

According to one example, this characteristic parameter can be the actual value of the time response of the medium to an external electromagnetic field at a certain moment in time during the state of the artificial kinetics. For example, this time moment can be chosen when the response attains its asymptotic or almost asymptotic magnitude of the time response, e.g., at the moment of 1 minute after applying the external electromagnetic field. For instance, for the photo-acoustic measurements, the external electromagnetic field can be light, having the wavelengths selected from the range of 500–1700 nm; while for the impedance measurements, the external electromagnetic field can be ac electromagnetic field having the frequency selected from the range of 1–200 MHz.

According to another example, this characteristic parameter can be a parametric slope (PS) defined as the ratio between a first function depending on a response of the medium corresponding to one wavelength (frequency) of the external electromagnetic field and a second function depending on the response of the medium corresponding to another wavelength (frequency). For instance, one of the wavelengths (frequencies) can always be selected in the glucose sensitive range, e.g. between 700–780 nm for the photo-acoustic measurements, and 1–200 MHz for impedance measurements; while the other wavelength (frequency) can be taken either from the glucose sensitive range or outside of this range.

According to one embodiment, the first and second functions can be logarithmic functions $\log(T_1)$ and $\log(T_2)$ of the responses $T_1$ and $T_2$, corresponding to the two different wavelengths (frequencies). According to another embodiment, the first and second functions can be functions of the time rate of the changes of the light response signal, i.e., $\Delta T/\Delta t$ (or $\Delta \log T/\Delta t$), where $\Delta t$ can be any part of the time interval during which the condition of artificial kinetics is maintained or altered.

It should be appreciated that the characteristic parameter utilized for calculation of the blood characteristics can be calculated as a function of various parameters obtained from more than one technique. For example, the characteristic parameter can be calculated as a predetermined relationship between the parameters obtained from photo-acoustic measurements in combination with impedance measurements.

According to the invention, for determining a desired blood characteristic, certain reference data sensitive to patient individuality should be provided. The reference data should be indicative of the desired blood characteristic (e.g., glucose concentration) as a function of the characteristic parameter derived as described above. Such reference data can, for example, be a calibration curve defining the dependence of the characteristic parameter on the desired blood characteristic. The calibration curve can be created by plotting a dependence of the characteristic parameter versus the desired blood characteristic that can be obtained for the particular individual or various patients by any other known invasive or non-invasive method which is independent of the current measurements. It should be appreciated that for different blood characteristics such independent methods may also be different. For example, a calibration curve to be used for determining the glucose concentration may be constructed by measuring the concentration of glucose in the blood by an invasive method simultaneously with the method of the present invention. Such measurements for constructing the calibration curve can be carried out either for a specific patient during a certain time period, sufficient to observe changes of the concentration of his glucose, or by applying measurements to various patients having different glucose concentration. It should be appreciated that when required (e.g., for increasing accuracy of the measurement), a combination of several techniques can be used for obtaining a calibration curve.

Figure 6:
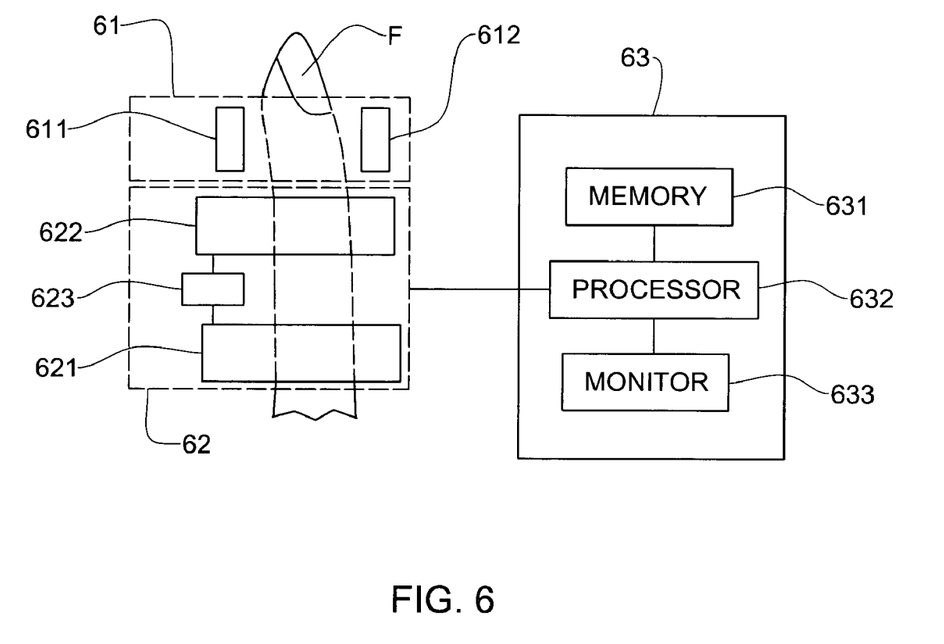
FIG. 6 illustrates a schematic block diagram of a measuring system for carrying out the method of the present invention, according to one embodiment of the invention.

Referring to FIG. 6, a schematic block diagram of a measuring system 60 applied to a patient's finger F for carrying out the method of the present invention is illustrated. It should be noted that the blocks in FIG. 6 are intended as functional entities only, such that the functional relationships between the entities are shown, rather than any physical connections and/or physical relationships. Although the application of the measuring system to the patient's finger F will be illustrated below, it should be understood that other parts of the patient's body, e.g., a toe, a wrist, an elbow and/or a knee, can also be used, *mutatis mutandis*, as a medium for the light transmission measurements. The system 60 comprises such main constructional parts as a measuring probe 61, a pressurizing assembly 62 (occluder), and a control unit 63. The measuring probe 61 includes a source 611 of an external electromagnetic field configured for applying the field to the blood perfused fleshy medium (i.e., finger F), and a detecting module 612 configured for measuring the response of the medium to the external field.

According to one embodiment of the invention, the measuring probe 61 can be a photo-acoustic system that may be any known photo-acoustic system configured for irradiating the medium and detecting the generated acoustic energy. According to another embodiment of the invention, the measuring probe 61 can be any conventional system for measuring impedance of the medium and/or components of the impedance. According to a further embodiment of the invention, the measuring probe 61 includes a combination of a photo-acoustic system and a system for measuring impedance of the medium. According to yet a further embodiment of the invention, the measuring probe 61 includes a combination of a photo-acoustic system, a system for measuring impedance of the medium and any other system. An example of another system includes, but is not limited to, a photo-optical system described in U.S. Pat. No. 6,400,972, International Applications WO 01/45553 and WO 01/96872, all assigned to the assignee of the present application.

Numerous examples of the photo-acoustic and impedance measuring systems are well known in the art (see, for example, EP 0 282 234; U.S. Pat. Nos. 6,466,806; 6,049,728; 5,792,668; WO 00/43759; WO 02/069791), and therefore the detail of these systems will not be expounded herein below.

The pressurizing assembly 62 includes a primary occlusion cuff 621 operable for applying the primary over-systolic pressure to the patient's finger F at a location $L_1$ and, when required, a secondary occlusion cuff 622 operable for applying the secondary pressure to the patient's finger at a location $L_2$ in the vicinity of a measurement location ML. The pressurizing assembly 62 further includes a pressure driver 623 actuated by the control unit 64 for operating the squeezing of the cuff 621 and, when required, the cuff 622. The primary occlusion cuff 621 and the secondary occlusion cuff 622 may be of any known suitable type. It should be noted that the primary occlusion cuff 621 may, for example, be accommodated on the patient's wrist or palm, while the secondary occlusion cuff 622 and the detecting module 612 of the probe 61 (measuring either an acoustic response or impedance of the medium) may be located on the patient's finger.

Preferably, the location $L_2$ is selected downstream of the main occlusion (location $L_1$) with respect to the normal blood flow direction. Generally speaking, the locations to which the pressure and measurements are applied should preferably be aligned along the direction of the normal blood flow. It should be also noted that the measurement location ML may, for example, be accommodated so as to coincide with the location of applying the secondary pressure or slightly differ from it, depending on the kind of measured medium and/or design of the measuring probe 61.

A signal detected by the measuring probe 61 is fed to the control unit 63 through a suitable electronic interface block, typically including an analog-to-digital (A/D) converter (not shown) configured for generating measured data indicative of time evolutions of the response of the medium. The control unit 63 is interconnected between the measuring probe 61 and the pressurizing assembly 62 for synchronizing the operation of the source 611 of the external field and the pressure driver 623 so as to apply primary over-systolic pressure to a certain location on the medium for creating a condition of artificial blood kinetics in the medium at the measurement location and maintaining this condition for a certain time period. Likewise, when required, the control unit 63 can provide synchronization for applying secondary pressure to the fleshy medium in the vicinity of or at the measurement location so as to alter the condition of artificial blood kinetics over a predetermined time interval within the certain time period, and thereby modulating the properties of blood affecting the time response. The control unit 63 is coupled to the output of the detecting module 612 for applying the measurements synchronously while maintaining and/or altering the condition of the artificial blood kinetics.

The control unit 63 includes a computer device having such known utilities as a memory 631 for storing, inter alia, reference data sensitive to patient individuality and indicative of the desired blood characteristic(s) as a function of a characteristic parameter derived, as have been described above, from the response of the medium. The control unit 63 further includes a processor 632 (data acquisition and processing utility), and a monitor 633 configured for presenting the measurement results. The processor 632 is preprogrammed by a suitable software model capable of analyzing the received output of the detecting module 612 (measured data) and determining one or more desired characteristics of the patient's blood by utilizing the reference data, as have been described above.

Those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Also, it is to be understood that the phraseology and terminology employed herein are for the purpose of description and should not be regarded as limiting.

In the method claims that follow, alphabetic characters numerals used to designate claim steps are provided for convenience only and do not imply any particular order of performing the steps.

Finally, it should be noted that the word "comprising" as used throughout the appended claims is to be interpreted to mean "including but not limited to".

It is important, therefore, that the scope of the invention is not construed as being limited by the illustrative embodiments set forth herein. Other variations are possible within the scope of the present invention as defined in the appended claims and their equivalents.

The invention claimed is:

1. A non-invasive method for use in determining at least one desired characteristic of blood of a patient, the method comprising:
   (a) creating a condition of artificial blood kinetics at a measurement location in a patient's blood perfused fleshy medium and maintaining this condition for a certain time period;
   (b) applying an external electromagnetic field to the measurement location;
   (c) detecting a time response of the medium from at least a portion of the measurement location to said external electromagnetic field, the response including at least one of an acoustic response to illuminating incident light having a wavelength in a range where the scattering properties of blood are sensitive to light radiation or an impedance of the portion of the medium;
   (d) generating measured data indicative of time evolutions of the response of the medium over at least a part of said certain time period;
   (e) analyzing said measured data for determining at least one characteristic parameter derived from said time response of the medium, the characteristic parameter including at least one of an actual value of the time response at a certain moment, during said certain time period, chosen when the response attains its near asymptotic magnitude; and a parametric slope defined as a ratio between a first function depending on a time response of the medium corresponding to a first frequency of the external electromagnetic field or a second function depending on the time response of the medium corresponding to a second frequency;

(f) providing predetermined reference data sensitive to patient individuality and indicative of the desired blood characteristic obtained by other independent method as a function of said at least one characteristic parameter; and (g) utilizing the determined characteristic parameter derived from said time response of the medium and said predetermined reference data for obtaining a value of the desired blood characteristic.

2. The method of claim 1 further comprising:
altering said condition of the artificial blood kinetics at the measurement location over a predetermined time interval within said certain time period so as to modulate properties of the blood affecting said time response.

3. The method of claim 2 wherein said altering of the condition of artificial blood kinetics includes applying a perturbation to the medium by at least one secondary pressure pulse of a predetermined value over said predetermined time interval.

4. The method of claim 3 wherein the predetermined value of the secondary pressure is in the range of about 0–300 mmHg.

5. The method of claim 2 wherein said altering of the condition of artificial blood kinetics includes applying a perturbation to the medium by secondary pressure of a predetermined cyclic pattern over said predetermined time interval.

6. The method of claim 5 wherein said predetermined cyclic pattern is in the form of secondary pressure pulses having amplitudes in the range of about 0–300 mmHg.

7. The method of claim 1, wherein said reference data is a calibration curve defining a dependence of the characteristic parameter on the desired blood characteristic.

8. The method of claim 1, wherein said first and second functions are logarithmic functions of the response corresponding to the first and second frequencies, respectively.

9. The method of claim 1, wherein said first and second functions are a time rate of the changes of the response corresponding to the first and second frequencies, respectively.

10. The method of claim 1 wherein said creating of the condition of artificial kinetics includes applying primary over-systolic pressure to a certain location at the medium with a normal blood flow upstream of the measurement location so as to achieve a state of temporary blood flow cessation in the medium at the measurement location.

11. The method of claim 1 wherein said certain time period is insufficient for irreversible changes in the fleshy medium.

12. The method of claim 1 wherein said at least one desired characteristic of the patient's blood is a concentration of glucose therein.

13. A system for non-invasive determination of at least one desired characteristic of blood of a patient, the system comprising:

(i) a pressurizing assembly arranged for creating a condition of artificial blood kinetics at a measurement location in a patient's blood perfused fleshy medium and at least maintaining this condition for a certain time period, the pressurizing assembly comprising a primary occlusion cuff for applying a primary over-systolic pressure to the fleshy medium at a primary pressure location, and a secondary occlusion cuff for applying a secondary pressure to the flesh medium at a secondary pressure location, thereby altering the condition of the artificial blood kinetics at said secondary pressure location over a predetermined time interval within said certain time period so as to modulate properties of the blood affecting said time response;

(ii) a measuring probe including
a source of an external electromagnetic field configured for applying said external electromagnetic field to said measurement location, and
a detecting module configured for detecting a time response of the medium from at least a portion of the measurement location to said external electromagnetic field; and (iii) a control unit electrically coupled to said pressurizing assembly, said control unit including:
a memory for storing reference data sensitive to patient individuality and indicative of the desired blood characteristic as a function of a characteristic parameter derived from said time response; and
a data acquisition and processing utility coupled to the detecting module for receiving and analyzing measured data therefrom and configured to utilize the reference data and determine said at least one desired blood characteristic.

14. The system of claim 13 wherein said primary pressure location is selected upstream of the secondary pressure location with respect to the normal blood flow direction in the medium, said secondary pressure location being in the vicinity of the measurement location.

15. The system of claim 13 wherein said measuring probe includes a photo-acoustic system, where said source of the external electromagnetic field being configured for generating a light beam in the wavelength range where the scattering or absorbing properties of the patients blood are sensitive to provide an acoustic response, and where said detecting module is an acoustic detector.

16. The system of claim 13 wherein said measuring probe includes a system for measuring impedance of at least a portion of the medium at the measurement location.

17. The system of claim 13 wherein said reference data is a calibration curve defining a dependence of the characteristic parameter on the desired blood characteristic.

18. The system of claim 17 wherein said at least one characteristic parameter is an actual value of the time response at a certain moment during said certain time period.

19. The system of claim 18 wherein said certain moment is chosen when the response attains its near asymptotic magnitude.

20. The system of claim 13 wherein said characteristic parameter is a parametric slope defined as a ratio between a first function depending on a time response of the medium corresponding to a first frequency of the external electromagnetic field and a second function depending on the time response of the medium corresponding to a second frequency.

21. The system of claim 20 wherein said first and second functions are logarithmic functions of the response corresponding to the first and second frequencies, respectively.

22. The system of claim 20 wherein said first and second functions are a time rate of the changes of the response corresponding to the first and second frequencies, respectively.

23. The system of claim 13 wherein said at least one desired characteristic of the patient's blood is a concentration of glucose therein.

24. A system for non-invasive determination of at least one desired characteristic of blood of a patient, the system comprising:

(i) a pressurizing assembly arranged for creating a condition of artificial blood kinetics at a measurement location in a patient's blood perfused fleshy medium and at least maintaining this condition for a certain time period;

(ii) a measuring probe comprising a source of an external electromagnetic field configured for applying said external electromagnetic field to said measurement location, said source of the external electromagnetic field being configured for generating a light beam in the wavelength range where the scattering or absorbing properties of the patients blood are sensitive to provide an acoustic response, and a detecting module comprising an acoustic detector configured for detecting a time response of the medium from at least a portion of the measurement location to said external electromagnetic field; and (iii) a control unit electrically coupled to said pressurizing assembly, said control unit comprising a memory for storing reference data sensitive to patient individuality and indicative of the desired blood characteristic as a function of a characteristic parameter derived from said time response; and a data acquisition and processing utility coupled to the detecting module for receiving and analyzing measured data therefrom and configured to utilize the reference data and determine said at least one desired blood characteristic.

25. The system of claim 24 wherein said pressurizing assembly includes a primary occlusion cuff for applying a primary over-systolic pressure to the fleshy medium at a primary pressure location.

26. The system of claim 25 wherein said pressurizing assembly further includes a secondary occlusion cuff for applying a secondary pressure to the flesh medium at a secondary pressure location, thereby altering said condition of the artificial blood kinetics at said secondary pressure location over a predetermined time interval within said certain time period so as to modulate properties of the blood affecting said time response.

27. The system of claim 26 wherein said primary pressure location is selected upstream of the secondary pressure location with respect to the normal blood flow direction in the medium, said secondary pressure location being in the vicinity of the measurement location.

28. The system of claim 24 wherein said measuring probe includes a system for measuring impedance of at least a portion of the medium at the measurement location.

29. The system of claim 24 wherein said reference data is a calibration curve defining a dependence of the characteristic parameter on the desired blood characteristic.

30. The system of claim 29 wherein said at least one characteristic parameter is an actual value of the time response at a certain moment during said certain time period.

31. The system of claim 30 wherein said certain moment is chosen when the response attains its near asymptotic magnitude.

32. The system of claim 24 wherein said characteristic parameter is a parametric slope defined as a ratio between a first function depending on a time response of the medium corresponding to a first frequency of the external electromagnetic field and a second function depending on the time response of the medium corresponding to a second frequency.

33. The system of claim 32 wherein said first and second functions are logarithmic functions of the response corresponding to the first and second frequencies, respectively.

34. The system of claim 32 wherein said first and second functions are a time rate of the changes of the response corresponding to the first and second frequencies, respectively.

35. The system of claim 24 wherein said at least one desired characteristic of the patient's blood is a concentration of glucose therein.

\* \* \* \* \*